United States Patent [19]

Gross et al.

[11] Patent Number: 4,787,655

[45] Date of Patent: Nov. 29, 1988

[54] AIRTIGHT CONNECTION FOR BREATHING CIRCUITS

[75] Inventors: James R. Gross, St. Charles, Ill.; Edward R. Tasher, Long Beach, Calif.

[73] Assignee: The Kendall Company, Boston, Mass.

[21] Appl. No.: 856,076

[22] Filed: Apr. 24, 1986

[51] Int. Cl.⁴ .............................................. F16L 41/00
[52] U.S. Cl. .................... 285/151; 285/273; 285/921; 128/205.24; 128/207.16
[58] Field of Search ............. 285/273, 274, 281, 190, 285/151, 152, 921, 207.16; 128/205.24

[56] References Cited

U.S. PATENT DOCUMENTS

| | | | |
|---|---|---|---|
| 1,920,610 | 8/1933 | Timbs | 285/281 X |
| 2,073,255 | 3/1937 | Schaetzly | 285/151 X |
| 2,820,651 | 1/1958 | Phillips | 285/151 |
| 3,334,926 | 8/1967 | Fallow | 285/151 X |

FOREIGN PATENT DOCUMENTS 71553 10/1950 Denmark ............................ 285/190

Primary Examiner—Dave W. Arola
Attorney, Agent, or Firm—Donald N. Halgren

[57] ABSTRACT

The invention comprises a swivel adapter for a ventilator breathing system serving an incapacitated patient. The swivel adapter utilizes a pair of corrugated hoses which mate with a pair of arms which are permitted to swivel on the body of the adapter. A ribbed collar is disposed on the body of the adapter and receives an endo-tracheal tube inserted within the trachea of the patient. A locking means secures the branches of the body to the swivelable arms of the adapter, and a circumferential sealing means, in the form of an 'o'-ring is disposed between the branch and its receiving orifice in its respective arm, to permit secure swiveling thereof, while preventing leakage of any gases therefrom.

5 Claims, 2 Drawing Sheets

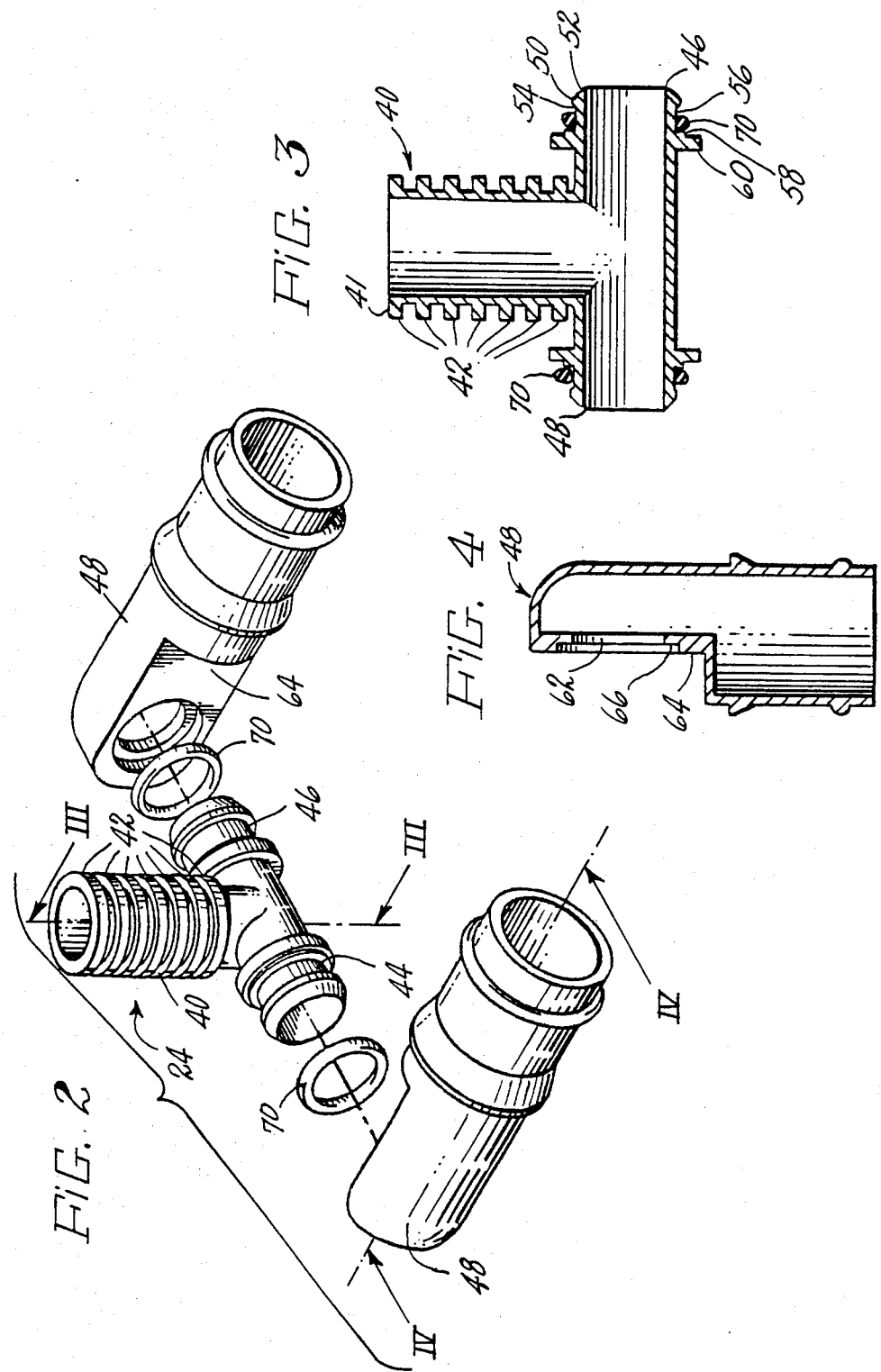

AIRTIGHT CONNECTION FOR BREATHING CIRCUITS

BACKGROUND OF THE INVENTION

2. Field of the Invention

This invention relates to breathing circuits and more particularly to wye junctions for those breathing circuits.

2. PRIOR ART

A breathing system may be defined as an assembly of tubing that provides passage of the flow of respiratory gases between a ventilator or anesthesia machine and a patient. The breathing system includes a tracheal tube, the tracheal tube connector, a breathing tube or tubes, adapters and other components sometimes used within the assembly such as humidifiers, monitoring spirometers, airway pressure monitors, oxygen analyzers and end tidal $CO_2$ analyzers.

These breathing systems maybe utilized to assist or sustain patients by mechanical ventilation, either in conjunction with surgical anesthesia or in long-term ventilatory support. Examples of systems such as this may be seen in U.S. Pat. Nos. 4,240,417 and 4,463,755.

In these breathing systems however, disconnection may sometimes result, leading to an injury or death. The causes of such accidental disconnection are complex and are such as to relatively rarely cause an injury. Disconnection events are fairly common in critical care and is anesthesia. They occur principally at or immediately adjacent the tracheal tube connection to the rest of the breathing system.

Other U.S. Patents which show an attempt to deal with the junctures of tracheal tubes are shown in U.S. Pat. Nos. 4,475,548 and 4,346,702.

While recommendations for snug or tight interfitting connectors or wyes have been made they are at best awkward to use and may interfere with convenience to the patient or to the caring personnel. Other problems with a standard friction fit connection include the possibility of leakage at these joints, which would most certainly effect other personnel inasmuch as the gases being transported within these tracheal tubes may be any type of anesthetic including halothene, isothane or even ether. Any leakage of these gases would certainly have a detrimental effect on medical personnel adjacent the patient being treated.

It is thus an object of the present invention to provide a wye interconnection arrangement in a breathing circuit which is articulatable to permit portions thereof to swivel according to the needs of the patient and of the administrator.

It is a further object of the present invention to provide an interconnection arrangement for a breathing system which is articulatable with one hand.

It is yet a further object of the present invention to provide a interconnecting means for a breathing circuit which will not permit the escape of gaseous fluids passing therewithin.

It is still yet another object of the present invention to provide a swivel assembly interconnection device which will not come apart when moved or swiveled in a normal course of a patient's movement.

BRIEF SUMMARY OF THE INVENTION

A breathing system for connecting a patient to a mechanical ventilator for either long-term ventilation or for anesthesia delivery comprising a tracheal tube which is used to provide fluid communication to the patient, a tracheal tube connector which is attached to the tracheal tube, an adapter assembly, and an arrangement of breathing tubes which are usually corrugated in nature and extend in fluid communication from the adapter to a expiratory valve or an inspiratory valve as part of the breathing circuit. The adapter comprises a swivel wye tee and two swivel wye arms attached thereto, the swivel wye arms each being in fluid communication with the corrugated breathing tubes leading to the valves. The swivel wye tee has a central body portion which interconnects with the tracheal tube connector. The body of the swivel wye tee has a plurality of longitudinally disposed rings or ribs for assisting the gripping between an anesthesia mask and the swivel wye tee. The swivel wye tee has a pair of opposed branches which are each in fluid communication with the body of the swivel wye tee. Each branch has a flange at its distalmost end. Each flange has a bevel face on its distalmost edge. The flange has a shoulder which steps radially inwardly towards a first peripheral portion. Proximal from the first peripheral portion is a second shoulder, which is contiguous to a main flange. The main flange is disposed about the periphery of the branch.

The shoulder of the distalmost flange engages the inside wall of the opening on the swivel wye arms. An 'o'-ring is disposed about the first peripheral portion and is caused to be pressed between the second shoulder and the outside wall of the opening on the swivel wye arm. The 'o'-ring comprises the sealing means, while the proximal side of the beveled flange, which flange is press-fit through the orifice in the wye arms, provides the locking interrelationship therebetween.

BRIEF DESCRIPTION OF THE DRAWINGS

The objects and advantages of the present invention will become more apparent when viewed in conjunction with the following drawings in which:

FIG. 2 is an exploded view of a swivel wye assembly;

FIG. 3 is a side elevational view taken along the lines III—III of FIG. 2; and

FIG. 4 is a sectonal view taken along the lines IV—IV of FIG. 2.

DESCRIPTION OF THE PREFERRED EMBODIMENTS

Figure 1:
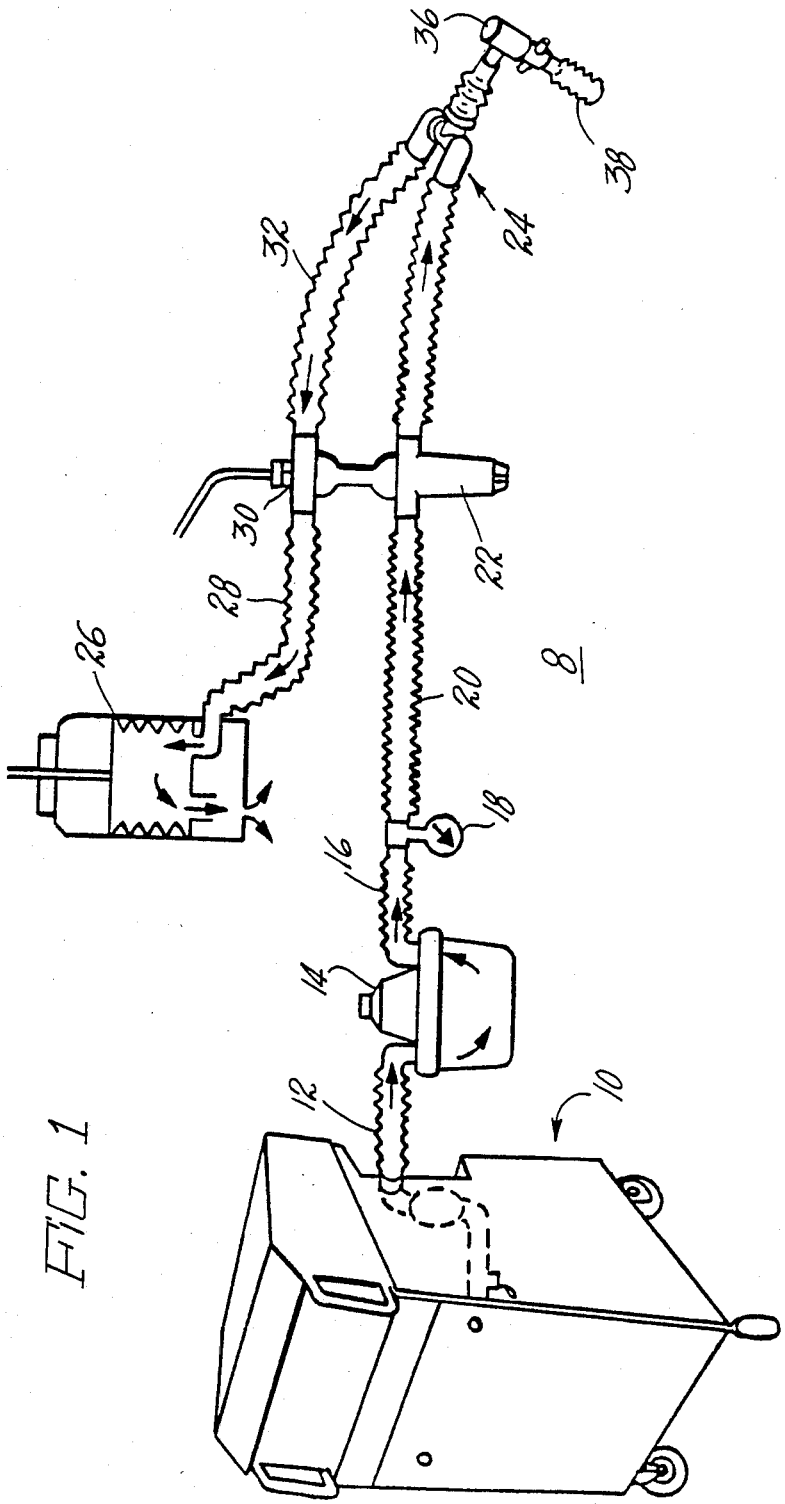
FIG. 1 is an overall view of a ventilator breathing system.

Referring now to the drawings in detail and more particularly to FIG. 1, there is shown a typical ventilator breathing system 8 comprising a ventilator machine 10 in fluid communication through a corrugated hose 12 with a humidifier device 14. The humidifier device 14 is in fluid communication through a further corrugated hose 16 to a airway pressure gage 18 thence through another corrugated hose 20 to a nebulizer 22. A corrugated hose 23 connects the nebulizer 22 to a swivel wye assembly 24 which comprises the invention of this application. Another branch of the ventilator breathing system includes a spirometer 26 which receives exhaled gases through a corrugated hose 28 which is passed through a exhalation valve 30 which receives gases through a further corrugated hose 32 which itself is also connected to the swivel wye assembly 24. The swivel wye assembly 24 has a body portion which is connected to an elbow adapter 36 which connects to a tracheal tube 38 which may enter the patient. The swivel wye assembly 24 is shown more particularly in FIG. 2. The swivel wye connector 24 comprises a swivel wye tee member 40 of hollow configuration having a plurality of ribs or rings 42 arranged coaxially about its central body portion. The rings 42 serve to act as gripping means to facilitate attachment of an anesthesia mask thereto, (not shown). The tee member 40 has opposed branches 44 and 46 which are in fluid communication with the hollow body portion 40. Each branch 44 or 46 is matable and in fluid communication with a swivel wye arm 48. Each arm 48 is hollow to provide fluid communication to the body 40 of the tee member 24 to the corrugated tubes. A sealing means 70 is disposed near the distal end of each branch 44 and 46 where it engages each swivel wye arm 48. The swivel wye tee member 40 is shown in cross section in FIG. 3. The central body portion 41 is shown in fluid communication with each branch 46 and 48. Each branch 46 or 48 has a flange 50 on its distalmost edge. Each flange 50 has a beveled distalmost surface 52. The distalmost flange 50 has a shoulder 54 which meets a circumferential surface 56 which extends to an annular "shoulder" ring 58 on the distalmost side of a main proximal flange ring 60. The sealing means 70 which may comprise an 'o'-ring is disposed about the circumferential surface 56, as shown in FIG. 3.

The swivel wye arm 48 is shown in cross section along its longitudinal axis, in FIG. 4. The arm 48 is hollow and is generally of cylindrical configuration. The arm 48 is attachable at its proximal end through an orifice 62 disposed across a planar surface 64 arranged on the proximal end of the arm 48. The orifice 62 has a shoulder cut-out 66 therearound.

Each branch 44 or 46 is arranged so as to be engageable through the orifice 62 in its respective wye arm 48. The flange 50 on each branch 48 or 46 thereon extends into the wye arm 48. The shoulder 54 on the proximal side of flange 50 is arranged to slidingly and rotatably engage the inner wall surface adjacent the periphery of the orifice 62 of its wye arm 48. The sealing means 70 is disposed against the shoulder 66 on the wye arm 48 and is arranged so as to encircle the periphery 56 and seal longitudinally against the shoulder 58 on the proximal flange 60.

Each sealing means 70 arranged between the locking engagement means on each of the branches 44 or 46 permits the wye member 40 to be articulatable with respect to its arms 48. The sealing member 70, in this case, preferably a resilient rubber 'o'-ring, prevents any leakage of gas from the breathing system which gas might be detrimental to those personnel and the medical care facility in which the system is being used. The interlocking arrangement of the flanges within the wye arm permits the arms to be freely moved for the convenience of the patient and the operating personnel.

Thus there has been shown a swivel wye assembly for use in a ventilator breathing system, which swivel wye assembly permits a free flow of gases through the system while it prevents leakage thereof detrimental to the patient and to the personnel therewith. The articulation of the arms of the swivel wye assembly permits convenience and adaptation into the assembly.

We claim:

1. A swivel adapter for a ventilator breathing system to permit a patient to inhale and exhale gases through a plurality of independent movable arrangeably disposable conduits, said adapter comprising:
    a swivel wye tee member having a hollow central body member;
    a pair of hollow branch members disposed across one end of said central body member, and in fluid communication therewith;
    a locking means disposed on the end of each of said branches;
    a hollow cylindrically shaped arm having an orifice through a sidewall thereof into which a branch member extends, said locking means of said branch engaging the inner side of said sidewall to securely lock yet permit articulation between each of said branches and said arms; and
    a sealing means disposed about each of said branches to prevent gases leaking out of the juncture between said branches and said arms, while also permitting the free swiveling between said arms.

2. A swivel adapter as recited in claim 1, wherein said sealing means comprises a resilient 'o'-ring disposed outwardly of said orifice and circumferentially disposed about said branch.

3. A swivel adapter as recited in claim 2, wherein said orifice on said arm has circumferential shoulder which receives said 'o'-ring.

4. A swivel adapter as recited in claim 3, wherein said branch has a sealing flange thereon, with a circumferential shoulder disposed thereon to provide a longitudinal bias on said 'o'-ring.

5. A swivel adapter as recited in claim 4, wherein said 'o'-ring is pressed into the wall of said circumferential shoulder to provide said sealing means therebetween.

* * * * *